United States Patent [19]
Cady et al.

[11] Patent Number: 6,066,092
[45] Date of Patent: May 23, 2000

[54] PREEMPTIVE PROPHYLAXIS OF MIGRAINE DEVICE AND METHOD

[76] Inventors: Roger K. Cady, 631 Riverview Rd.; Kathleen U. Farmer, 225 Finley Dr., both of Ozark, Mo. 65721

[21] Appl. No.: 09/185,310

[22] Filed: Nov. 3, 1998

Related U.S. Application Data

[60] Provisional application No. 60/064,879, Nov. 6, 1997.

[51] Int. Cl.[7] .................................................. A61B 5/00
[52] U.S. Cl. ............................................ 600/300; 128/920
[58] Field of Search .................................... 600/300, 301; 128/920, 923

[56] References Cited

U.S. PATENT DOCUMENTS

| | | |
|---|---|---|
| 4,816,470 | 3/1989 | Dowle et al. . |
| 5,037,845 | 8/1991 | Oxford . |
| 5,840,018 | 11/1998 | Michaeli .................................. 600/300 |

OTHER PUBLICATIONS

J. N. Blau, *Migraine: Clinical, therapeutic, conceptual and research aspects*, London, Chapman and Hall, 1987, pp. 4–7.

Roger K. Cady, *Treating the Headache Patient*, Ch. 6 New York, Marcel Dekker, Inc., 1995, pp. 101–118 121–122.

D. Reeves, et al., ANAM V3.11a/96 User's Manual, 1996 Update 1997, pp. 1,10–14,16–28,32–35.

IMITREX Tablets leaflet, Feb. 1997.

*Migraine Today*, Migraine Information Center.

*Primary Examiner*—Cary O'Connor
*Assistant Examiner*—Navin Natnithithadha
*Attorney, Agent, or Firm*—Husch & Eppenberger, LLC; Robert E. Muir

[57] ABSTRACT

A preemptive prophylaxis migraine method uses the following cognitive tests: Simple Reaction Time; Running Memory Continuous Performance Task; Matching to Sample; Mathematical Processing Task; and interprets the results as a percent of baseline indicator of need for prophylaxis. A preemptive prophylaxis migraine device includes a microprocessor having a memory; the aforementioned cognitive tests loaded into the memory; means for computing the score on a trial of these tests to establish a baseline, for storing the baseline in the memory, for computing the score of a subsequent trial of the tests, and for comparing the same to the stored baseline; and means for indicating a cognitive change.

20 Claims, 3 Drawing Sheets

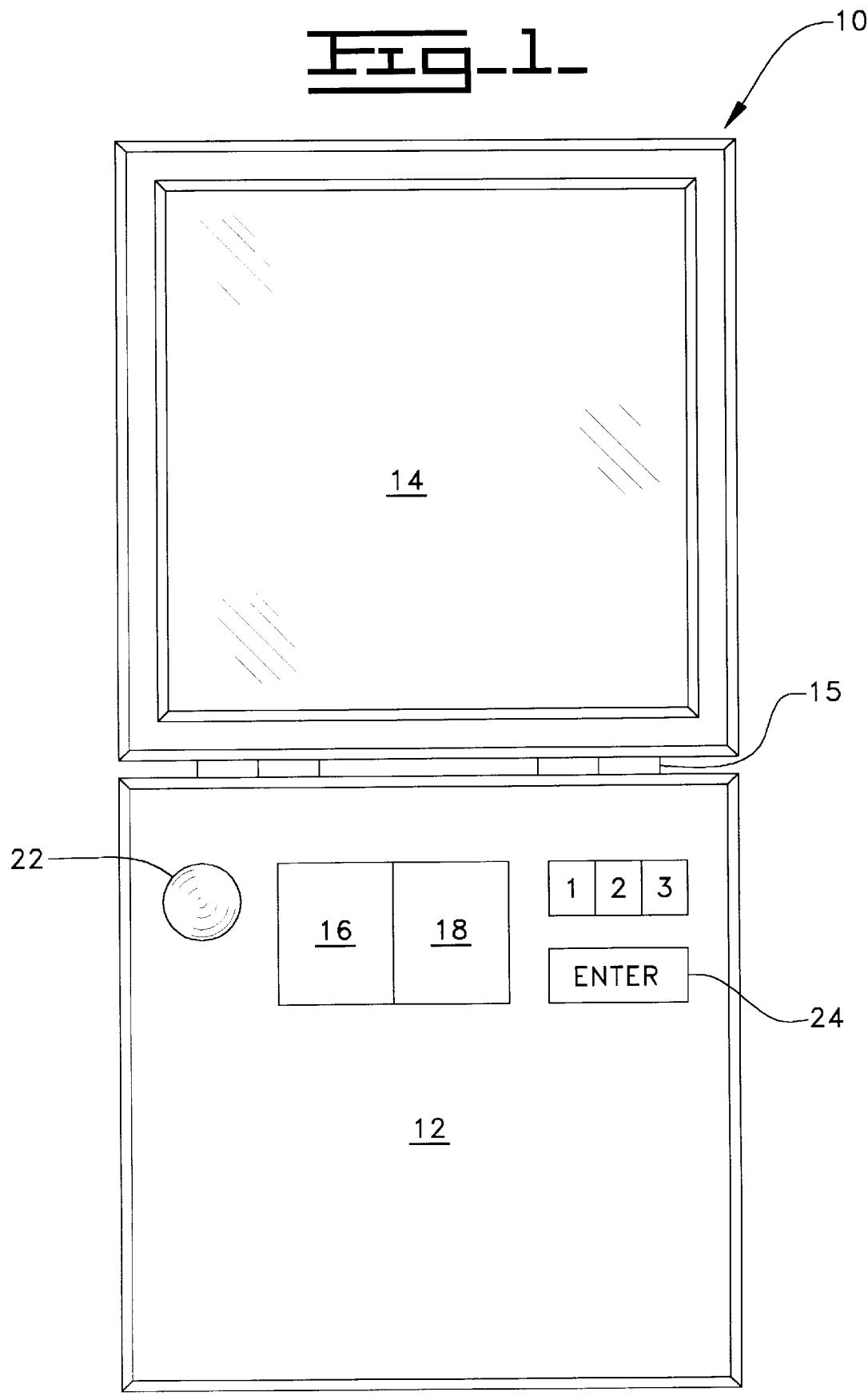

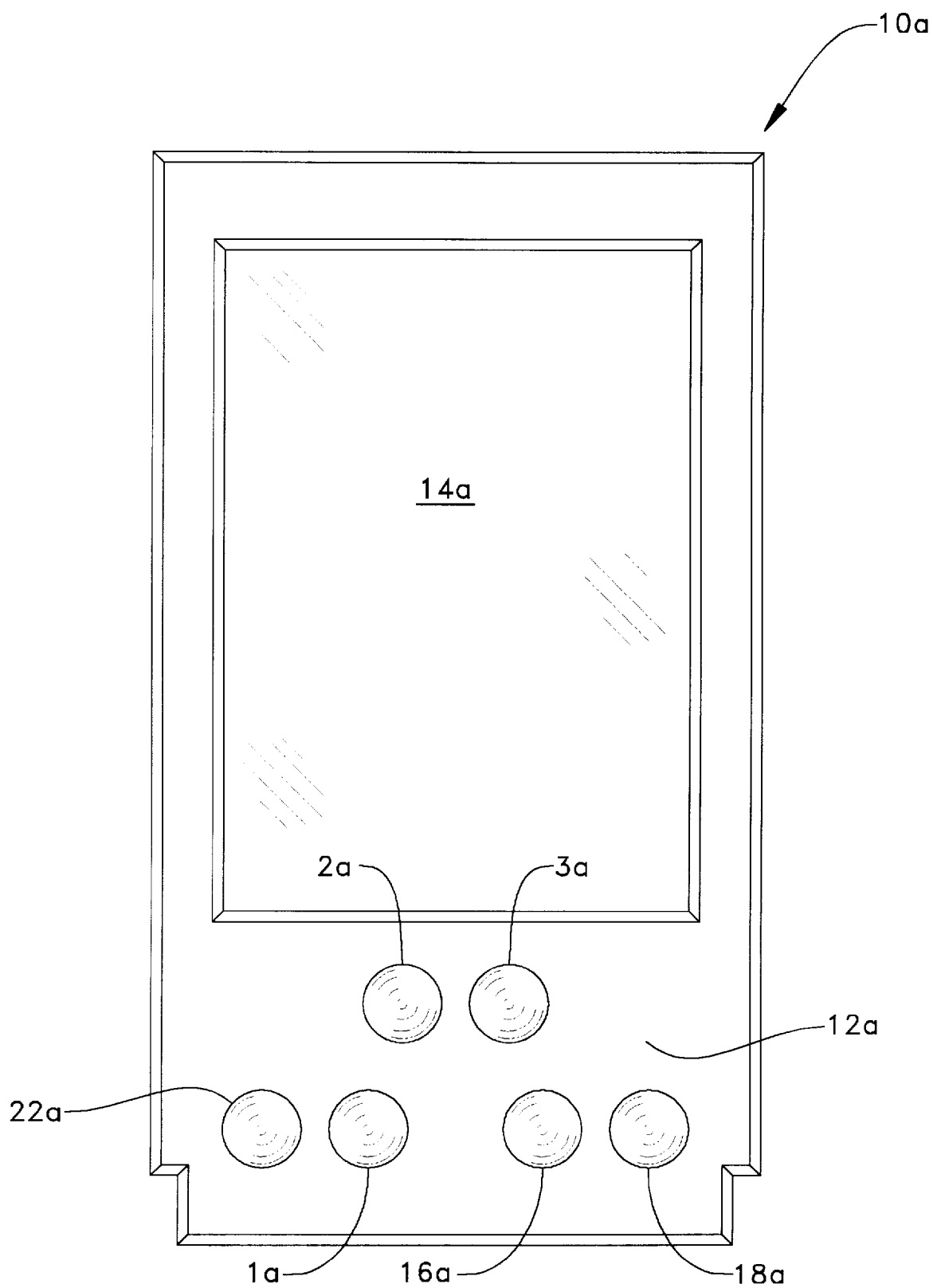

PREEMPTIVE PROPHYLAXIS OF MIGRAINE DEVICE AND METHOD

CROSS REFERENCE

This application claims priority of prior Provisional Application Ser. No. 60/064,879, filed Nov. 6, 1997.

BACKGROUND OF THE INVENTION

The present invention relates generally to the health field and more particularly to a device and method for predicting the onset of a migraine headache.

A headache may be one of several different varieties, each of which has its own unique pain characteristics which differ dramatically. The types of headache include tension, sinus, cluster, rebound and migraine. Migraine is a particularly painful headache that recurs from time to time. The pain is quite severe and often the person with migraine must stay in bed. Dietary, emotional and environmental factors may trigger an attack. On average, migraine sufferers experience an attack a month. Attacks last from four to seventy-two hours. Migraine sufferers sometimes get a warning signal before an attack. Some experience "aura," a disruption of brain function that occurs twenty to thirty minutes before the attack. This is characterized by visual disturbances like flashing lights and blurred vision. Other common symptoms include numbness or a tingling feeling around the lips or hands, hallucinations and loss of speech. Other migraine sufferers get a "prodrome," which occurs several hours or even a day before an attack. The symptoms may include yawning, fatigue, mood changes, food cravings, and sensitivity to light, sound, touch, or odors. Of interest is that the incidence of migraine appears to be on the rise. Because of the severity and incidence of migraine, prescription medicines have been invented to provide relief. One is sumatriptan succinate sold under the trademark IMITREX by Glaxo Wellcome Inc. and covered by U.S. Pat. Nos. 4,816,470 and 5,037,845. A leaflet included with IMITREX instructs the migraine sufferer to take a tablet as soon as the symptoms of migraine appear. It is desirable to be able predict the onset of migraine before the head pain actually occurs and thereby permit the prophylactic administration of medicine.

The Automated Neuropsychological Assessment Metrics (ANAM) is a set of standardized batteries of cognitive tests, modified by neuropsychologists in the U.S. Armed Forces for precise measurement of cognitive processing efficiency of military personnel. The tests assess sustained concentration and attention, mental flexibility, spatial processing, cognitive processing efficiency, mood, arousal/fatigue level, and short-term, long-term and working memory. The ANAM is now in the public domain. The most recent version is ANAM V3.11 a/96 which includes the following battery of tests:

1. Subject Demographics Form
2. Stanford Sleepiness or Sleep/Fatigue Scale
3. Mood Scale 2
4. Simple and Two-Choice Reaction Time
5. Sternberg Memory Search Tasks
6. Running Memory Continuous Performance Task
7. Mathematical Processing Task
8. Digit Set Comparison Task
9. Logical Reasoning-Symbolic
10. Tower of Hanoi (Tower Puzzle)
11. Stroop Color/Word Interference
12. Code Substitution (Letter/Symbol Comparison)
13. Code Substitution (Immediate and Delayed Recall)
14. Spatial Processing Task (Simultaneous)
15. Matching to Sample
16. Tapping (Left and Right Index Finger)
17. Modified Orientation and Amnesia Test It would be desirable to be able to use a subset of these tests to predict the onset of migraine.

The present invention is directed to meeting one or more of the above-stated desirable objectives.

SUMMARY OF THE INVENTION

In accordance with one aspect of the invention there is provided a preemptive prophylaxis migraine method using the following cognitive tests: Simple Reaction Time; Running Memory Continuous Performance Task; Matching to Sample; Mathematical Processing Task; and interpreting the results as a percent of baseline indicator of need for prophylaxis. Preferably the tests are administered in the listed sequence. Advantageously the tests are preceded by the Stanford Sleepiness Scale and Mood Scale 2 tests.

In accordance with another aspect of the invention there is provided a special purpose microprocessor by which the above tests may be taken by a migraineur. Preferably the device includes two mouse buttons and records performance on the tests. Advantageously the device is a handheld computer with a fold down screen or a palm-top type computer.

In a preferred arrangement there is provided a preemptive prophylaxis migraine device including a microprocessor having a memory, a battery of tests loaded into the memory of the microprocessor and including a Simple Reaction Time, a Running Memory Continuous Performance Task, a Matching to Sample, and a Mathematical Processing Task; means for computing the score on a trial of these tests to establish a baseline and for storing the baseline in the memory; the means for computing being operative for computing the score of a subsequent trial of the tests and comparing the same to the stored baseline; and means for indicating a cognitive change.

Other aspects and advantages may be perceived from the following description.

BRIEF DESCRIPTION OF THE DRAWINGS

The accompanying drawings illustrate two devices and one method for carrying out the present invention and wherein:

FIG. 1 is a plan view of a hand-held computer which is one embodiment of the invention;

FIG. 1A is a plan view of a palm-top type computer which is another embodiment of the invention.

DETAILED DESCRIPTION

Figure 2:
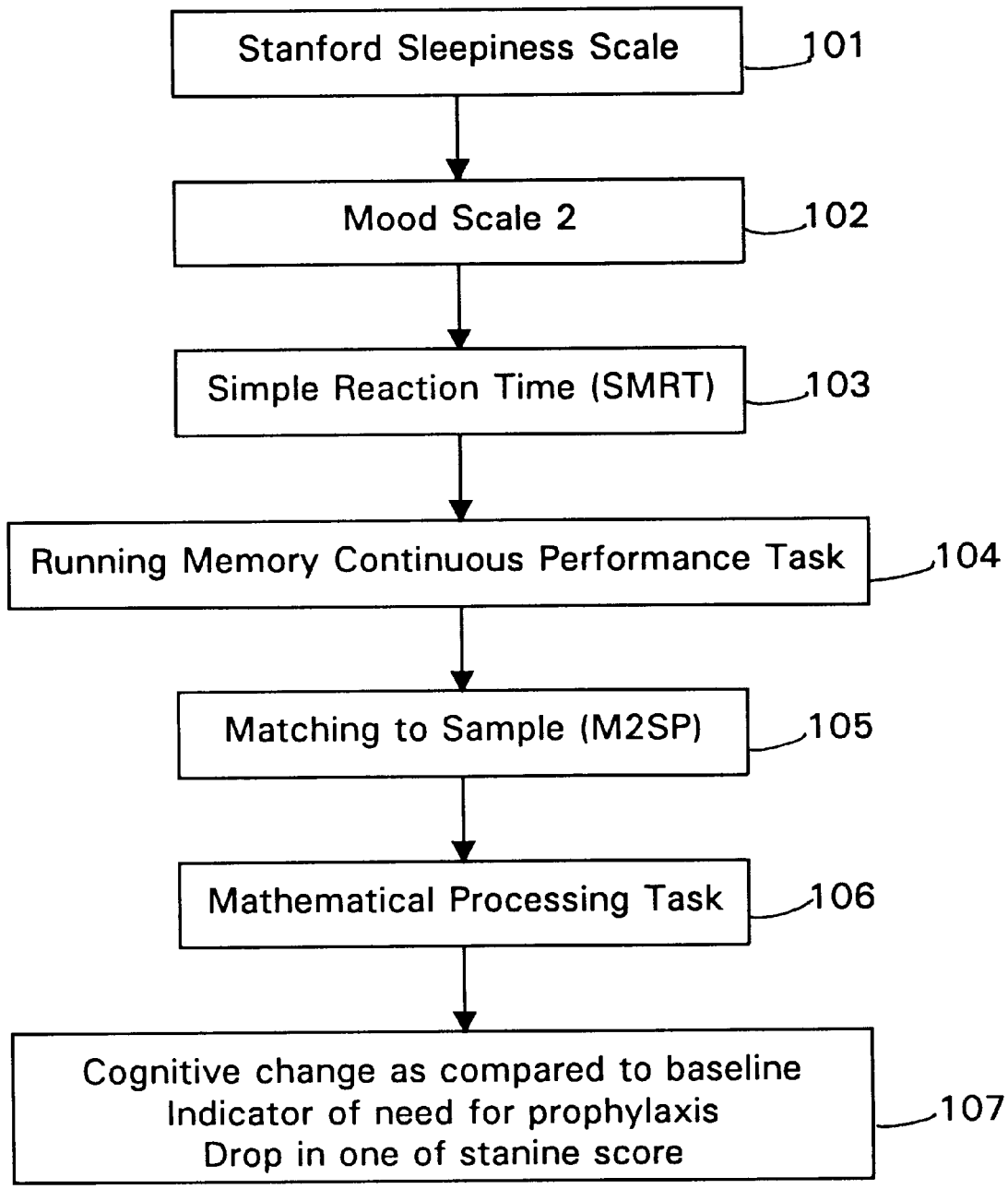
FIG. 2 is a flow chart illustrating the steps and sequence of a method for performing preemptive prophylaxis of migraine.

FIG. 1 shows a preemptive prophylaxis of migraine device in the form of a hand-held computer, generally designated 10, and having a key pad 12 and a screen 14 which advantageously is at least four inches (10.16 cm.) square. A hinge 15 is provided so the screen 14 may be conveniently folded down upon the key pad 12 for storage or transporting. When open the computer 10 is conveniently about 5"×9" (12.7 cm. by 22.86 cm.) in size. The key pad 12 has a built-in set of two mouse buttons 16,18, a start/stop or on/off button 22, an enter key 24, and Mood Scale 2 keys 1, 2 and 3. As used herein the terms "buttons" and "keys" are intended to mean the same thing. The computer 10 contains memory chips (not shown) which have a set of programmed cognitive tests 103–106 (hereafter described) and which record a person's performance time in milliseconds on those tests. The computer program uses the score in milliseconds on the third trial of these cognitive tests as a baseline measurement, which is converted to a stanine score. Subsequent trials are similarly scored and converted to stanine.

FIG. 1A shows a palm-top type computer 10*a* which, when programmed with the cognitive tests 103–106, performs the same functions as hand-held computer 10. Accordingly, the same functional parts identified in FIG. 1, are identified in FIG. 1A with the same numerals and the letter "a". Further description is deemed unnecessary. It is believed that the largest palm-top computer now available is 7.8 inches (19.81 cm.) long and the screen 14*a* is not as large as the desired four inches (10.16 cm.) square. However, this deficiency is offset by the savings in using mass produced devices.

FIG. 2. shows the sequence of the method. From the seventeen tests of the original ANAM, four subtests were selected and sequenced for measuring cognitive processing efficiency of migraine sufferers, as follows:

1. Simple Reaction Time (SMRT), 103
2. Running Memory Continuous Performance Task (CPT), 104
3. Matching to Sample (M2SP), 105
4. Mathematical Processing Task (MATH), 106

Also included are two preliminary measures of alertness and mood that are also part of the ANAM:

1. Stanford Sleepiness Scale, 101
2. Mood Scale 2, 102

Description of Subtests:

1. The first step 101 is Stanford Sleepiness Scale which consists of seven statements that describe the present state of alertness or sleepiness and are numbered from one to seven, with one being highly alert and seven being close to sleep. Individuals rate their level of alertness prior to taking the first subtest of the battery. It provides a way to monitor fatigue over the course of repeated measures. Subjective ratings may be correlated with measured performance.

2. The second step 102 is Mood Scale 2 which consists of a list of thirty-six adjectives that are rated on a three-point scale. Using mouse button 16 participants respond to each adjective by indicating "yes," "moderately," or "no," based on how they feel at the present time. The Mood Scale 2 categories include anger, happiness, fear (anxiety), depression, activity, and fatigue.

3. The third step 103 is Simple Reaction Time (SMRT) which presents a simple stimulus on the screen (*). In response, the individual presses the mouse button 16 each time the stimulus appears. The Reaction Time measures the speed of the motor response, the peripheral nerve conduction velocity. This represents the "hardware" of the nervous system in terms of input, followed by motor response. Actual cognitive processing time is not involved in this test.

4. The fourth step 104 is Running Memory Continuous Performance Test (CPT) which is a continuous letter comparison task. A randomized sequence of upper-case letters, A through Z, is presented one at a time in the center of the computer screen 14. The person presses button 16 if the letter on the screen matches the letter that immediately preceded it; and different button 18 if the letter on the screen is different than the immediately preceding letter. The task lasts approximately five minutes. The CPT was specifically designed to assess components of memory, attention, efficiency and consistency. This task is forced paced, with individuals having only a brief time in which to respond.

5. The fifth step 105 is Matching to Sample (M2SP) and consists of a number of trials that begins with a first design being presented in the center of the screen 14 for three seconds, followed by a showing that contains two designs. The person matches one of the two designs with the first design or sample by pressing the appropriate button 16 or 18. The design is a 4×4 checkerboard and varies by the number of cells that are shaded from one cell through twelve cells.

6. The sixth step 106 is Mathematical Processing (MATH) and involves arithmetic problems presented in the middle of the screen 14. Working from left to right, the person solves the addition and subtraction and decides if the answer is greater or less than the number 5.

As indicated, the scores are recorded by the computer 10 and the score on the third trial of these sequenced cognitive tests 103–106 are used as the baseline measurement. Subsequent trials measure cognitive change as compared to baseline. A drop of one in stanine score is an indicator of the onset of migraine and an indicator of need for prophylaxis. This was empirically determined by the following research. The preemptive prophylaxis of migraine method was used to measure cognitive deficiency during a migraine in each of a group of ten migraineurs. The method was used to measure the return of cognitive efficiency after injection of sumatriptan, an anti-migraine medication, in each of the group of ten migraineurs. The method measured cognitive change, compared to the baseline stanine score, that predicted the onset of a migraine.

The above described preemptive prophylaxis of migraine device and method allows a migraine sufferer to take medication to preempt the occurrence of head pain, associated symptoms and accompanying disability.

The invention in its broader aspects is not limited to the specific steps and apparatus shown and described, but departures may be made therefrom within the scope of the accompanying claims without departing from the principles of the invention and without sacrificing its chief advantages.

I claim:

1. A preemptive prophylaxis migraine method including the steps of:

performing the cognitive tests of: a Simple Reaction Time, a Running Memory Continuous Performance Task, a Matching to Sample, and a Mathematical Processing Task;

establishing a baseline indicator from the performed tests;

repeating the tests; and interpreting the results of the repeated tests as a percent of the baseline indicator of need for prophylaxis.

2. A preemptive prophylaxis migraine method as set forth in claim 1, wherein the step of establishing a baseline indicator uses a trial other than the first trial of the performed tests.

3. A preemptive prophylaxis migraine method as set forth in claim 2, wherein the trial used to establish the baseline indicator is the third trial.

4. A preemptive prophylaxis migraine method as set forth in claim 1, wherein the step of establishing a baseline indicator includes measuring the score in milliseconds.

5. A preemptive prophylaxis migraine method as set forth in claim 4, wherein the step of establishing a baseline indicator includes converting the score in milliseconds to stanine.

6. A preemptive prophylaxis migraine method as set forth in claim 5, wherein the step of repeating the tests includes converting the scores of the repeated tests to stanine.

7. A preemptive prophylaxis migraine method as set forth in claim 6, including the step of administering an anti-migraine medication when the repeated test stanine differs from the baseline stanine.

8. A preemptive prophylaxis migraine method as set forth in claim 1, wherein the cognitive tests are performed in the order listed.

9. A preemptive prophylaxis migraine method as set forth in claim 1, wherein the listed cognitive tests are preceded by a Stanford Sleepiness Scale test.

10. A preemptive prophylaxis migraine method as set forth in claim 1, wherein the listed cognitive tests are preceded by a Mood Scale 2 test.

11. A preemptive prophylaxis migraine method as set forth in claim 1, wherein the listed cognitive tests are preceded by a Stanford Sleepiness Scale test and a Mood Scale 2 test; the cognitive tests are performed in the order listed; the step of establishing a baseline indicator uses the third trial of the cognitive tests; the step of establishing a baseline indicator includes measuring the score in milliseconds and converting the same to stanine; the step of repeating the tests includes converting the scores of the repeated tests to stanine; and including the step of administering an anti-migraine medication when the repeated test stanine differs from the baseline stanine.

12. A preemptive prophylaxis migraine device including a microprocessor having a memory, a battery of tests loaded into the memory of the microprocessor and including a Simple Reaction Time, a Running Memory Continuous Performance Task, a Matching to Sample, and a Mathematical Processing Task; means for computing the score on a trial of these tests to establish a baseline and for storing the baseline in the memory; the means for computing being operative for computing the score of a subsequent trial of the tests and comparing the same to the stored baseline; and means for indicating a cognitive change.

13. A preemptive prophylaxis migraine device as set forth in claim 12, wherein the means for computing includes changing the scores to stanine.

14. A preemptive prophylaxis migraine device as set forth in claim 13, wherein the means for indicating a cognitive change is operative upon a drop of one in stanine score as compared to baseline.

15. A preemptive prophylaxis migraine device as set forth in claim 12, including a screen which is about 10 cm. square.

16. A preemptive prophylaxis migraine device as set forth in claim 12, including a screen and a key pad adjacent the screen.

17. A preemptive prophylaxis migraine device as set forth in claim 16, including means for hinging the screen and key pad so that they may be folded upon each other.

18. A preemptive prophylaxis migraine device as set forth in claim 16, wherein the key pad includes a plurality of mouse buttons.

19. A preemptive prophylaxis migraine device as set forth in claim 16, wherein the key pad includes a plurality of Mood Scale 2 buttons.

20. A preemptive prophylaxis migraine device as set forth in claim 16, wherein the key pad includes an on/off button, two mouse buttons, and three Mood Scale 2 buttons.

* * * * *